(12) United States Patent
Holt et al.

(10) Patent No.: US 7,955,826 B2
(45) Date of Patent: Jun. 7, 2011

(54) COMPOSITION AND METHODS FOR IMPROVING THE PRODUCTION OF FERMENTATION OPERATIONS

(75) Inventors: Jason Holt, Acworth, GA (US); Christopher B. Murphy, Woodridge, IL (US); Jon O. Fabri, Charleston, SC (US)

(73) Assignee: Polymer Ventures, Inc., Charleston, SC (US)

( * ) Notice: Subject to any disclaimer, the term of this patent is extended or adjusted under 35 U.S.C. 154(b) by 52 days.

(21) Appl. No.: 11/818,859

(22) Filed: Jun. 15, 2007

(65) Prior Publication Data

US 2007/0292919 A1 Dec. 20, 2007

Related U.S. Application Data

(60) Provisional application No. 60/814,244, filed on Jun. 16, 2006.

(51) Int. Cl.
C12P 7/06 (2006.01)
(52) U.S. Cl. .................. 435/161; 435/151; 435/171
(58) Field of Classification Search .................. None
See application file for complete search history.

(56) References Cited

U.S. PATENT DOCUMENTS

| | | | | |
|---|---|---|---|---|
| 3,960,539 | A | 6/1976 | Newhall | 71/76 |
| 5,407,899 | A * | 4/1995 | Howell | 504/152 |
| 5,589,164 | A | 12/1996 | Cox et al. | 424/76.5 |
| 5,892,133 | A | 4/1999 | Ogura et al. | 568/832 |
| 5,972,411 | A | 10/1999 | Goldstein et al. | 426/600 |
| 5,998,335 | A | 12/1999 | Selga et al. | 504/353 |
| 6,114,298 | A | 9/2000 | Petri et al. | 510/372 |
| 6,218,336 | B1 | 4/2001 | Coleman | 504/118 |
| 6,306,450 | B1 | 10/2001 | Bank et al. | 426/534 |
| 6,319,523 | B1 | 11/2001 | Zhou | 424/725 |
| 6,387,933 | B1 | 5/2002 | Nakamura et al. | 514/345 |
| 6,509,297 | B1 | 1/2003 | Coleman | 504/127 |
| 6,545,043 | B1 | 4/2003 | Coats et al. | 514/514 |
| 6,663,860 | B1 | 12/2003 | Tvedten | 424/94.63 |
| 6,716,472 | B2 | 4/2004 | Goldstein et al. | 426/600 |
| 6,759,370 | B1 | 7/2004 | Innes | 504/142 |
| 6,767,972 | B1 | 7/2004 | Irick, Jr. et al. | 525/445 |
| 6,812,190 | B2 | 11/2004 | Coleman | 504/127 |
| 6,818,424 | B2 | 11/2004 | DiCosimo et al. | 435/166 |
| 6,860,232 | B2 | 3/2005 | Keithly et al. | 119/171 |
| 6,902,726 | B1 | 6/2005 | Varel | 424/76.6 |
| 6,969,696 | B2 | 11/2005 | Coleman | 504/118 |
| 6,974,685 | B2 * | 12/2005 | Muramatsu et al. | 435/155 |
| 7,018,641 | B1 | 3/2006 | Momol et al. | 424/405 |
| 7,048,952 | B2 | 5/2006 | Gerson et al. | 424/725 |
| 2003/0228402 | A1 * | 12/2003 | Franklin et al. | 426/541 |
| 2004/0044087 | A1 * | 3/2004 | Maye | 514/784 |

OTHER PUBLICATIONS

Winniczuk & Parish, Food Microbiology, 1997, vol. 14, p. 373-381.*
Umbreit et al., PNAS, USA, 1973, vol. 70, No. 10, p. 2997-3001.*
Grohmann et al., Applied Biochemistry and Biotechnology, 1994, vol. 45/46, p. 315-327.*
Lee et al., Biotechnology Letters, 1996, vol. 18, No. 3 p. 299-304.*
Institute of Chemistry, Dept. of Biology, University of Berlin, Terpenes, 2003, p. 1-3.*
Shenker et al., Biochemistry and Molecular Biology International, 1996, vol. 40, No. 1, p. 145-150.*
Uribe et al., Journal of Chemical Ecology,1990, vol. 16, No. 4, p. 1399-1408.*
Lee et al., Biotechnology Letters, 1996, vol. 18, No. 3 p. 299-304.*
Grohmann et al. , Applied Biochemistry and Biotechnology, 1994, vol. 45/46, p. 315-327.*
Shenker et al., Biochemistry and Molecular Biology International, 1996, vol. 40, No. 1, p. 145-150.*
U.S. Patent Publication No. 2006/0199739 A1, Pub. Date Sep. 7, 2006, Messerschmidt et al.
U.S. Patent Publication No. 2004/0248764 A1, Pub. Date Dec. 9, 2004, Franklin.
U.S. Patent Publication No. 2003/0194454 A1, Pub. Date Oct. 16, 2003, Bessette et al.
Denise Abrahim et al., *Effects of Four Monoterpenes on Germination, Primary Root Growth, and Mitochondrial Respiration of Maize*, J. Chem. Ecol., vol. 26., No. 3, 2000, pp. 611-624.
Yumei Liu, et al., *Characterization of the Chinese SA-1 Hop (Humulus lupulus L.)* Variety, MBAA TQ, vol. 43, No. 2, 2006, pp. 136-138.
Val E. Peacock, et al., *Chemistry of Hop Aroma in Beer*, ASBC Journal, vol. 39, No. 4, pp. 136-141.
Hop Aroma and Flavor, *The Essential Oil of Hops: Hop Aroma and Flavor in Hops and Beer*, http://www.realbeer.com/hops/aroma.html (downloaded Jun. 6, 2006).
Val E. Peacock, et al., *Fate of Hop Oil Components in Beer*, ASBC Journal, vol. 46, No. 4, pp. 104-107.
Hopunion LLC, *HOPUNION*, http://www.hopunion.com/hop-use-products.shtml (downloaded Jun. 6, 2006).
Institute of Chemistry, Department of Biology, Chemistry, Pharmacy, FU Berlin, *Terpenes*, http://www.chemie.fu-berlin.de/chemistry/oc/terpene/terpene_en.html (downloaded Jun. 6, 2006).
Chemical Compound Outline (Part I), *Major Types of Chemical Compounds in Plants & Animals*, http://waynesword.palomar.edu/chemid1.htm (downloaded Jun. 6, 2006).

* cited by examiner

*Primary Examiner* — Kade Ariani
(74) *Attorney, Agent, or Firm* — Marshall, Gerstein & Borun LLP

(57) ABSTRACT

Methods and compositions for improving the production of ethanol by a *Saccharomyces* spp. yeast in a fermentation medium are provided, where the method comprises adding to the fermentation medium an emulsion comprising a monoterpene and a surfactant in an amount sufficient to improve the production of ethanol.

20 Claims, 1 Drawing Sheet

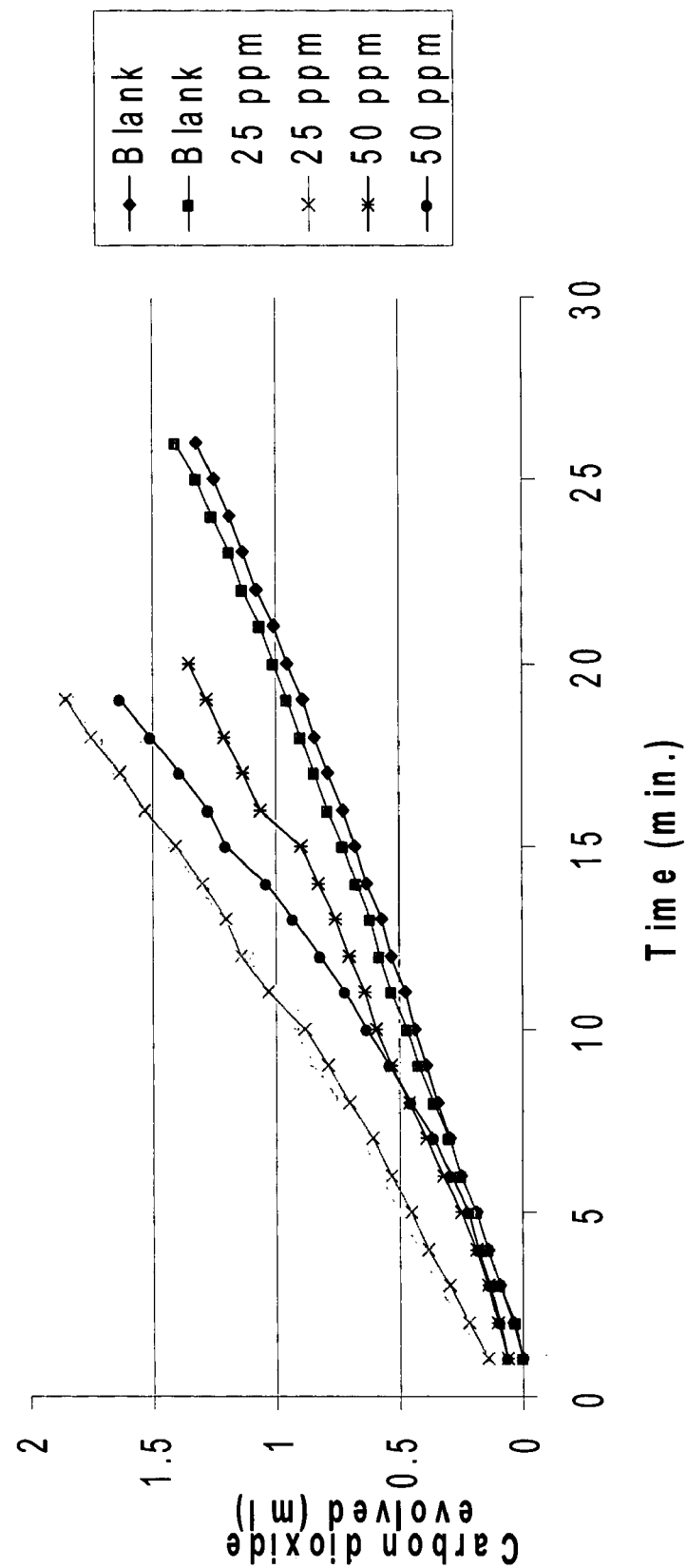

COMPOSITION AND METHODS FOR IMPROVING THE PRODUCTION OF FERMENTATION OPERATIONS

This application claims priority to U.S. Provisional Patent Application Ser. No. 60/814,244, filed Jun. 16, 2006, which is incorporated in its entirety herein by reference.

BACKGROUND OF THE INVENTION (1) Field of the Invention

The present invention relates to compositions and methods for the improvement of fermentations, and more particularly to compositions and methods for the improvement of the rate, yield, maintenance requirements, and/or other parameters of fermentation operations.

(2) Description of the Related Art

The production and processing of foods, feeds, chemicals and pharmaceuticals by fermentation is well known. The metabolic activities of bacteria, yeasts, fungi, and mixtures of these organisms have been used for thousands of years to modify compounds and to produce new compounds. Raising of bread dough, fermentation of beer and wine, curing of olives, pickles and cheese, cleaning of cocoa and coffee, reduction of indigo and retting of flax are all fermentations with long histories.

More recently, fermentations have been used to produce industrial chemicals, such as ethanol, acetone, butanol, organic acids, as well as enzymes, proteins and special carbohydrates. Microorganisms are also used to produce secondary metabolites, such as penicillin, erythromycin, and other antimicrobial substances, which are the basis of modern antibiotics.

Most modern fermentations are carried out in fermentation vessels under more or less sanitary conditions and under more or less rigorous environmental controls. Some pharmaceutical fermentations for example are maintained under strict sanitation and in pure cultures, while other fermentations, such as for wine and spirits, have more relaxed sanitation requirements.

As with any production operation, fermentation economics depend upon factors such as the yield of a desired product per unit of raw material (substrate) utilized, the rate of production of the desired product per unit of volume of the fermentation vessel, the amount of and cost of other nutrients and supplies that are required by the fermentation, and the length of time the fermentation can be operated without shutdown for maintenance and cleaning.

A fermentation operation that has been increasing in importance is the production and recovery of ethyl alcohol (ethanol) for use as fuel. Ethanol that is produced by fermentation for fuel use has been referred to as bioethanol. In commercial bioethanol production, a starch feedstock, typically corn, is hydrolyzed with enzymes such as amylase to convert complex polysaccharides such as starch into simple sugars that can be metabolized by the fermenting microorganism—usually a yeast such as *Saccharomyces cerevisiae*. The degraded feedstock is then subjected to anaerobic fermentation to convert the sugars to ethanol and carbon dioxide. A reported yield for conversion of corn to ethanol is 2.5 gallons ethanol per bushel (25 kg) of corn. The actual yield is lower than theoretical due to the inefficiency of the process, and any improvement in the efficiency would increase the effective yield. Based on the information in a U.S. Department of Energy Feasibility Assessment, the overall efficiency of the fermentation step is in the range of 80 to 90%.

Because ethanol for fuel use must be produced at a low cost, in most commercial bioethanol production plants the yeasts that are present in the fermenter at the end of a batch fermentation are recovered for recycle back into a new batch of medium. Due to cost restraints, it is impractical to use rigorous sanitation practices in bioethanol production and contaminating microorganisms, notably acid-producing bacteria, sometimes accumulate in the equipment and in the recycled charge of yeast. If the level of these contaminants rises to noticeable levels, they will convert sugars or ethanol into organic acids—thus lowering the yield of ethanol per unit of substrate. This situation usually requires treating the yeasts with antibiotics, or replacing the yeasts and shutting down and sanitizing the fermentation equipment. In plants that operate continuous-flow fermentations, it is not uncommon to see a build up of contaminating organisms in various parts of the lines or fermenters. This condition also requires plant shut down and sanitization and results in a reduction in plant productivity.

It would be useful to provide methods that would reduce the frequency of plant shutdowns for cleaning and sanitizing. It would also be useful if such methods increased the yield, rate, or productivity of the fermenter, or of the entire fermentation plant. Furthermore, it would also be useful it such methods were easy to administer, did not interfere with the operation of the fermentation plant, and were cost effective.

Terpenes are natural constituents of essential oils that are typically found in plants. Terpenes are based on five-carbon isoprene ($C_5H_8$) subunits and can optionally include aromatic rings. Many terpenes are hydrocarbons, but oxygen-containing alcohols, aldehydes and ketones, known as terpenoids, are also found. It is not uncommon for terpenes to be present in fermentations, especially in food and beverage fermentations in which natural plant products are used. But the primary purpose for their inclusion, when their addition is purposeful, is for the flavors and aromas that they add. An example of such a use is the addition of hops to beer fermentations.

The essential oil of hops contains the terpenes myrcene and β-pinene and the sesquiterpenes β-caryophyllene and α-humulene. Terpenoids such as linalool and geraniol and esters such as geranyl isobutyrate and methyl dec-4-enoate are also present. Hops are commonly added to hot wort in the brewkettle during wort boiling with the purpose of adding bitterness to the beer, supplying tannins to help precipitate unwanted proteins, improving beer stability due to antibacterial properties, and reducing the surface tension of the wort so that a vigorous boil can be maintained. See, e.g. The essential oil of hops: hop aroma and flavor in hops and beer, at http://www.realbeer.com/hops/aroma, Jun. 7, 2006. In addition, or as an alternative, hop extracts or concentrated hop oil can be added to the beer fermenter, or even to the beer after fermentation is complete. The content of hop oils in beer is not high, however, and is commonly 10 ppm, or less by weight of the finished beer.

Although terpenes are most commonly included in fermentations for flavor and aroma purposes, other uses have been reported. Muramatsu et al., in U.S. Pat. No. 6,974,685, teach a method for the production of prenyl alcohol, itself a mixture of predominantly diterpenes, by *Saccharomyces* yeast from sugars in the presence of an oil and optionally a terpene and/or a surfactant. If a terpene, such as squalene or tocopherol was used, it was added to the fermentation media in an amount of 0.01% or more, and preferably 1% or more. If a surfactant was used, non-ionic surfactants, such as polyethylene glycol-type surfactants, were preferred.

On the other hand, however, the inclusion of terpenes in fermentation medium has been reported to be undesirable. In U.S. Pat. No. 4,503,079, King et al. teach the benefits of stripping essential oils from citrus molasses in order to improve the ethanol yield during fermentation. Citrus oils, such as d-limonene and mono-cyclic terpenes, were steam stripped from citrus molasses prior to fermentation. The inventors stated that these materials are known to inhibit fermentation and teach that their removal provides an improved fermentable feed stock.

No reports have been found, however, of the beneficial use of terpenes in a fermentation that does not have a terpene as its primary product for any purpose other than as flavorants and/or aromatics.

SUMMARY OF THE INVENTION

Briefly, therefore the present invention is directed to a novel method of improving the production of a non-terpene organic compound by a microorganism in a fermentation medium, the method comprising adding to the fermentation medium a combination of a terpene and a surfactant. In one embodiment, the combination of the terpene and the surfactant is added in an amount sufficient to increase the rate and/or the yield of production of the non-terpene organic compound.

The present invention is also directed to a novel composition for increasing the rate of production and/or the yield of a non-terpene organic compound by a microorganism in a fermentation medium, the composition comprising a terpene, and a surfactant.

Among the several advantages found to be achieved by the present invention, therefore, may be noted the provision of methods and compositions that are useful in fermentative production of non-terpene products to reduce the frequency of plant shutdowns for cleaning and sanitizing, the provision of methods and compositions that increase the yield, rate, or productivity of the fermenter, or of the entire fermentation plant, and the provision of methods and compositions that are easy to administer, do not interfere with the operation of the fermentation plant, and are cost effective.

BRIEF DESCRIPTION OF THE DRAWINGS

FIG. 1 is a graph of carbon dioxide gas evolution as a function of time for yeast fermentation of glucose in fermentation media having 0, 25 ppm, and 50 ppm, by weight of a 3% terpene emulsion, and which shows that $CO_2$ evolution rate is increased in both the 25 ppm and 50 ppm samples over the rate of evolution in the blanks containing no terpene emulsion.

DETAILED DESCRIPTION OF THE PREFERRED EMBODIMENTS

In accordance with the present invention, it has been discovered that the production of a non-terpene organic compound by a microorganism in a fermentation medium can be improved by adding to the fermentation medium a combination of a terpene and a surfactant. In certain embodiments, it has also been found that the addition of the terpene/surfactant combination to fermentation medium in a fermentation plant can result in reduced cleaning requirements for the fermentation operation.

As used herein, the terms "improved production" means one or more of: higher yield of the non-terpene product, higher rate of production of the non-terpene product, decreased requirements for shutting down the fermentation equipment for cleaning or maintenance, decreased requirement for nutrients, lower cost of nutrients, reduced requirements for labor for operating or maintaining the process or the equipment, and changes in any other parameter that results in an overall improvement in rate, yield, or cost of the process of producing the non-terpene product.

The present methods and compositions have been shown to be capable of increasing the rate of fermentation in the initial stages of sugar fermentation by *Saccharomyces* sp. yeast by over 75%, and also to be able to help maintain the viability of yeasts at the end of a commercial ethanol fermentation by a significant amount. It is believed that these effects can result in improvements in the cost and ease of operation of fermentation operations, such as for bioethanol plants.

The present novel methods and compositions are useful in fermentations in which the primary product is a non-terpene organic compound. As used herein, the terms "primary product" mean the major product of the fermentation. A "non-terpene organic" compound is any organic compound that is not a terpene, as that term is defined below.

Non-terpene organic compounds that are produced by fermentations in which the present methods and compositions are useful include food and feed fermentations, fermentations that yield industrial chemicals and fermentations that yield pharmaceuticals. Examples of non-terpene organic food and feed compounds include, without limitation, beer, bread, cheese, cocoa, coffee, koji, monosodium glutamate, olives, pickles, sauerkraut, tea, vinegar, wine, whiskey, and vitamins such as ergesterol, riboflavin, Vit. A, Vit. $B_2$, and Vit. $B_{12}$. Examples of non-terpene industrial organic compounds include, without limitation, acetic acid, acetone, aspartic acid, 2,3-butanediol, n-butyl alcohol, carbon dioxide, citric acid, dextran, dihydroxyacetone, ethanol, fumaric acid, fusel oil, gallic acid, gluconic acid, glycerol, isoleucine, itaconic acid, 2-ketogluconic acid, 5-ketogluconic acid, kojic acid, lactic acid, lysine, succinic acid, tartaric acid, valine, yeast, and enzymes such as amylase, cellulose, diastase, invertase, maltase, zymase, and protease. Examples of pharmaceuticals that are non-terpene organic compounds include, without limitation, amphoterccin B, bacitracin, bleomycin, candicidin, capreamycin, cephaloterccin C, chloramphenicol, chlortetracycline, colistin, cycloheximide, cycloserine, dactinomycin, doxorubicin, erythromycin, gentamicin, griseofulvin, kanamycin, lincomycin, mithramycin, mitomycin C, neomycin, novobiocin, nystatin, oleandromycin, paromomycin, penicillins, polymycin, rifampin, spectinomycin, streptomycin, tetracycline, vancomycin, and viomycin.

The non-terpene organic compound can be one or more compounds selected from the group consisting of non-terpene organic acids, alcohols, aldehydes, ketones, enzymes, amino acids, and carbohydrates. In a preferred embodiment, the non-terpene organic compound is ethanol.

In some embodiments of the present method, it is preferred that the non-terpene organic compound is an industrial product rather than a food product. By way of example, ethanol for fuel or industrial use is an example of a non-food non-terpene organic compound, while ethanol in beer and wine would not be such a product.

It is believed that the present methods and compositions are useful when almost any type of microorganism is used for the fermentation. By way of example, the microorganism can be a yeast, bacteria, fungi, or a mixture of any of these. In a preferred embodiment, the microorganism is yeast, and a particularly useful yeast is a *Saccharomyces* spp. yeast, such as *Saccharocyces cerevisiae*.

In the present method, a combination of a terpene and a surfactant is added to the fermentation medium. As used herein, the terms "fermentation medium" are meant to include the liquid or semisolid medium in which or on which the microorganisms are grown. A typical fermentation medium commonly includes a substrate and nutrients. Substrates are commonly sugars or more complex carbohydrates that are metabolized by the microorganism to obtain energy and basic structural components, but can also be lipids and/or proteins. In some fermentations, hydrocarbons can serve as the substrate. Nutrients include sources of nitrogen, potassium and phosphorous, but can also include trace minerals, vitamins, growth factors, amino acids, and other complex compounds.

As mentioned briefly above, terpenes are unsaturated hydrocarbons that occur in most essential oils and oleoresins of plants. Terpenes are based on the isoprene unit ($C_5H_8$) and may be either acyclic or cyclic with one or more benzenoid groups. They are classified as monocyclic (diterpene), dicyclic (pinene), or acyclic. (myrcene) according to the molecular structure. Terpene derivatives (camphor, menthol, terpineol, borneol, geraniol, and the like) are called terpenoids; many are alcohols, but terpenoids can also include aldehydes and ketones. Terpenes can also be classified according to the number of isoprene units that are included in the compound. For example, monoterpenes, such as pinene, nerol, citral, camphor, menthol, and limonene, contain 2 isoprene units. Sesquiterpenes, such as nerolidol and farnesol, contain 3 isoprene units. Diterpenes, such as phytol and Vitamin $A_1$, contain 4 isoprene units. Triterpenes, such as squalene, contain 6 isoprene units. Tetraterpenes, such as carotene (provitamin$A_1$) contain 8 isoprene units.

In the present invention the terpene can be almost any terpene. In some embodiments, the terpene comprises a monoterpene, sesquiterpene, diterpene, triterpene, tetraterpene, or a mixture of these. In a preferred embodiment, the terpene comprises a monoterpene. Examples of useful monoterpenes include, without limitation, pinene, nerol, citral, camphor, menthol, limonene, and mixtures thereof. Examples of useful sesquiterpenes, without limitation, include nerolidol, farnesol, or a mixture of these. Examples of useful diterpenes include, without limitation, phytol, Vitamin $A_1$, or a mixture of these. Examples of useful triterpenes include, without limitation, squalene. Examples of useful tetraterpenes include, without limitation, carotene.

Terpenoids are also included as terpenes for the purposes of the present invention. The terpene of the present invention can also be supplied by compounds such as turpentine and pine oil.

The terpene can also contain other plant-derived chemical components such as fatty acids, triglycerides, sterols, rosins, and furanocoumarins. Preferably, the terpene contains 30-100% of its chemical composition as terpenes, on a weight basis of the organic plant derived components. More preferably, the terpene comprises 60-100% of its chemical structure as terpenes. It is more preferred that the terpene of the present invention comprises 90-100% of its chemical structure as terpenes. In some embodiments, it is preferred that the terpene be purified. As used herein, the term "purified" means that the terpene or mixture of terpenes has been purified and increased in concentration to any degree from the natural source in which it is found. By way of example, orange oil or turpentine are purified terpenes, because they contain terpenes in a higher concentration than oranges or pine trees, which are the natural sources for these compounds. In some embodiments, it is preferred that the terpene be "isolated and purified". As used herein, the terms "isolated and purified" mean that the terpene has been purified and increased in concentration from the natural source in which it is found and that the concentration of terpenes is at least about 80% by weight of the isolated and purified terpene.

In some embodiments it is preferred that the terpene comprises one or more compounds selected from pinene, nerol, citral, camphor, menthol, limonene, nerolidol, farnesol, phytol, geraniol, farnesol, Vitamin $A_1$, squalene, tocopherol, carotene (provitamin$A_1$), careen, linalool, turpentine, or mixtures thereof. In other embodiments, limonene is the preferred terpene. Limonene can be provided in almost any form and purity, as long as other components that are present are not harmful to the fermentation. Examples of limonene sources include citrus oils, such as orange oil, lemon oil, oil of Bergamot, and caraway, for example. A racemic mixture of d- and l-limonene is useful for the present invention. In some embodiments, d-limonene is preferred. Limonene that is useful in the present invention can be obtained from the plant sources noted above, or it can be purchased as, for example, Aldrich Product No. 18, 316-4 (Sigma-Aldrich, St. Louis, Mo.). D-limonene (CAS #5989-27-5) is available from Ashland Distribution Co., Columbus, Ohio; Expo Chemical Co., Inc., Houston, Tex.; Florida Chemical Co., Inc., Winter Haven, Fla.; KIC Chemicals Inc., Armonk, N.Y.; and Penta Manufacturing Co., Livingston, N.J.

The terpene of the invention can be used in different physical forms. For example, the terpene can be placed in a carrier vehicle that can take the form of a concentrated liquid, a mixture, or an emulsion. Examples of a concentrated liquid form include oleoresins, extracts, oils, plant distillates, pressates, and the like. Examples of the terpene mixtures include combinations of terpenes with surfactants which can improve dispersion or emulsification in aqueous media, or combinations with organic solvents as residue from extraction processes, as an extender, a diluent, or viscosity reducer. Examples of the terpene emulsion form include oil-in-water or water-in-oil emulsions. Preferably, the emulsion is an oil-in-water emulsion that is stabilized against separation with the assistance of surfactants. The emulsion can also optionally contain other organic solvents as residue from extraction processes, as an extender, a diluent, or viscosity reducer. Examples of the organic solvent include organic hydrocarbons containing about 7 to about 30 carbons; linear or branched alkanes, preferably from $C_8$ to about $C_{40}$, more preferably from $C_{10}$ to $C_{24}$, including, for example, octane, nonane, decane, undecane, dodecane, tridecane, tetradecane, hexadecane, heptadecane, octadecane, nonadecane, and the like; monounsaturated or polyunsaturated olefins, preferably $C_8$-$C_{40}$, more preferably $C_{10}$-$C_{24}$, alpha olefins, preferably linear alpha olefins, more preferably $C_8$-$C_{40}$ linear alpha olefins, yet more preferably $C_{10}$-$C_{24}$ linear alpha olefins, including for example, octene, nonene, decene, undecene, dodecene, tridecene, tetradecene, hexadecene, heptadecene, octadecene, nonadecene, and the like; polybutenes or polyisobutylenes; parrafin oil or mineral oil or wax; fatty esters, preferably lower alkyl ($C_1$-$C_4$) esters of fatty acids, more preferably the methyl ester of a vegetable oil such as methyl soyate; triglycerides from animal and vegetable sources; volatile organic liquids with atmospheric pressure boiling points in the range of about 50°-250° C., especially lower alcohols such as methanol, ethanol, propanol, isopropanol, butanol, isobutanol, and the like.

The terpene of the invention is preferably in the form of an emulsion. In one embodiment, the emulsion can contain from about 1% to about 70% terpenes based on the total weight of the emulsion. In a preferred embodiment, the emulsion contains from 2% to 20% terpenes. In a more preferred embodiment, the emulsion contains from about 3% to about 15% terpenes.

It is preferred that the terpene is used in the present method in combination with one or more surfactants. The surfactant(s) are used to reduce interfacial tension, allowing for the formation of small emulsion droplets. The small droplet size is preferred to minimize the rate of gravity separation of the phases of the emulsion. In one embodiment, the surfactant concentration is from about 0.2% to about 25% of the emulsion, based on the total weight of emulsion. In a preferred embodiment, the surfactant concentration in the emulsion is 1% to 20%. In a more preferred embodiment, the surfactant concentration in the emulsion is 2% to 10%.

The surfactant can be a single type, but it is preferred to use a combination of two or more surfactants. It is common to characterize surfactants by a hydrophile-lipophile balance value, also known as HLB value. Surfactants with a low HLB are more lipid loving and thus tend to make a water in oil emulsion while those with a high HLB are more hydrophilic and tend to make an oil in water emulsion. When combinations of surfactants are used, the weighted average of the individual surfactant components is used to calculate the HLB of the combination. The preferred surfactant combination for the emulsion has an HLB value of about 6 to about 25. More preferred is an HLB of 8 to 20. Yet more preferred is an HLB of 9 to 18. And even more preferred is an HLB of from 11 to 16.

Surfactants that are useful in the present invention include, without limitation, ethoxylated alcohols, ethoxylated carbohydrates, ethoxylated vegetable oils, polyethyleneglycols (PEG), polypropylene glycols (PPG), monoesters and diesters of PEG and PPG, ethoxylated amines, fatty acids, ethoxylated fatty acids, fatty amides, fatty diethanolamides, and the like. Examples of specific surfactants, and commercial sources, include oleyl alcohol 10 EO (Ethox Chemical), Tween 20 (Uniqema), stearyl alcohol 20 EO (Ethox Chemical), castor oil 80 EO (Ethox Chemical), castor oil 30 EO (Ethox Chemical), PEG 400 Dioleate (Ethox Chemical), tallow amine 5 EO (Akzo Nobel), Burco TME-S (Burlington Chemical), coconut diethanolamide (Ethox Chemical), Ethfac 161 (Ethox Chemical), cocoamine 2 EO (Akzo Nobel), cocoamine 5 EO (Akzo Nobel), Dowanol DB (Dow Chemical), Demulse DLN 532 CE (Deforest Enterprises), Tween 80 (Uniqema), Demulse DLN 622 EG (Deforest Enterprises), Span 20 (Uniqema), Diacid 1550 (Westvaco), decyl alcohol 4 EO (Ethox Chemical), dipropyleneglycol methyl ester (Dow Chemical), sodium lauryl sulfate (SLS), sodium dodecyl sulfate (SDS), sodium xylenesulfonate (SXS), and Tergitol NP6 (Dow Chemical).

An example of a useful combination of the terpene and the surfactant of the present invention comprises an emulsion comprising from about 1% to about 70% of a terpene, from about 0.2% to about 25% of a surfactant, all by weight, with the balance including water.

In another example, the combination of the terpene and the surfactant comprises an emulsion comprising from about 2% to about 20% of a terpene, from about 1% to about 20% of a surfactant, all by weight, with the balance including water.

In yet another example, the combination of the terpene and the surfactant comprises an emulsion comprising from about 3% to about 15% of a terpene, from about 2% to about 10% of a surfactant, all by weight, with the balance including water.

In an embodiment of the method of the invention, a terpene and surfactant combination is introduced into the fermentation medium in a fermentation for the production of a non-terpene organic compound. The terpene/surfactant combination is preferably added as a liquid, with batch, semibatch, or continuous addition. In one embodiment, the combination of the terpene and the surfactant is added to the fermentation medium before inoculation with the microorganism. The combination of the terpene and the surfactant can also be added to the fermentation medium during the first one-third of the fermentation. As used herein, the term "first one-third of the fermentation" refers to the first ⅓ of the total time of fermentation. In another embodiment, the combination of the terpene and the surfactant is added to the fermentation medium during the middle one-third of the fermentation, or the combination of the terpene and the surfactant is added to the fermentation medium during the final one-third of the fermentation. As used herein, the term "middle one-third of the fermentation" refers to the middle ⅓ of the total time of fermentation, and the term "final one-third of the fermentation" refers to the last ⅓ of the total time of fermentation. In some embodiments, the combination of the terpene and the surfactant is added to the fermentation medium in two or more increments during the fermentation.

The terpene/surfactant combination is introduced in an amount that is effective to increase the rate and/or the yield of the non-terpene organic compound product. By way of example, when the terpene/surfactant combination is provided as an emulsion having a composition such as is described above, the emulsion comprising the terpene and the surfactant is added to the fermentation medium in an amount of from about 0.1 ppm to about 1000 ppm, by weight. In another embodiment, the emulsion comprising the terpene and the surfactant is added to the fermentation medium in an amount of from about 1 ppm to about 100 ppm, by weight. In yet another example, the emulsion comprising the terpene and the surfactant is added to the fermentation medium in an amount of from about 5 ppm to about 50 ppm, by weight.

The rate or extent of production of the non-terpene organic compound by fermentation can be determined by taking measurements such as density, refractive index, calorimetry, chromatography, and gas evolution during the course of the fermentation process. An increase of the rate of production or of the final concentration of the product is desirable for maximizing the efficiency of the process. In a typical ethanol fermentation process, product yields of about 12% to about 14% ethanol, on a weight basis in the finished mixture are common. Although any increase in product yield or production rate, or in a reduction of maintenance requirements for the plant would be a benefit, a relative increase of 5% or more in the rate of ethanol production would be preferred. Also, a relative increase of 5% or more in the final ethanol concentration would be preferred. The terms "relative increase" are intended to distinguish a relative increase from an absolute increase. By way of example, an increase in final ethanol concentration from 12.5% to 13.1% would be a relative 5% increase, while an absolute increase of 5% would be an increase from 12.5% to 17.5%.

The present invention also includes a composition for improving the production of a non-terpene organic compound by a microorganism in a fermentation medium, the composition comprising a terpene and a surfactant. The composition of the invention can contain other adjuvants without departing from the scope of the invention. Examples of these adjuvants include preservatives, viscosity modifiers, solvents, wetting agents, tracing agents, dyes, and antifoams.

In a preferred embodiment of the present composition, the terpene comprises a monoterpene, sesquiterpene, diterpene, triterpene, tetraterpene, or a mixture of these. In another embodiment, the terpene comprises a monoterpene. The monoterpene can be selected from pinene, nerol, citral, camphor, menthol, limonene, and mixtures thereof. The terpene can also comprise a sesquiterpene. The sesquiterpene can be nerolidol, farnesol, or a mixture of these. The terpene can comprise a diterpene. The diterpene can comprise phytol, Vitamin $A_1$, or a mixture of these. In another embodiment, the terpene comprises a triterpene. The triterpene can be squalene. The terpene can comprise a tetraterpene, such as carotene.

It is preferred that the terpene of the terpene/surfactant composition comprises one or more compounds selected from pinene, nerol, citral, camphor, menthol, limonene, nerolidol, farnesol, phytol, geraniol, farnesol, Vitamin $A_1$, squalene, tocopherol, carotene (provitamin $A_1$), careen, linalool, turpentine, or mixtures thereof. In some instances, it is preferred that the terpene is a purified terpene, and in other instances it is preferred that the terpene is an isolated and purified terpene.

The surfactant of the terpene/surfactant composition can be one or more compounds selected from ethoxylated alcohols, ethoxylated carbohydrates, ethoxylated vegetable oils, polyethyleneglycols (PEG), polypropylene glycols (PPG), monoesters and diesters of PEG and PPG, ethoxylated amines, fatty acids, ethoxylated fatty acids, fatty amides, and fatty diethanolamides. It is preferred that the surfactant has a weighted average HLB value between about 6 and about 25, more preferred is an HLB value between about 8 and about 20, and even more preferred is an HLB value between about 9 and about 18.

Examples of useful surfactants include one or more of oleyl alcohol 10 EO, Tween 20, stearyl alcohol 20 EO, castor oil 80 EO, castor oil 30 EO, PEG 400 Dioleate, tallow amine 5 EO, Burco TME-S, coconut diethanolamide, Ethfac 161, cocoamine 2 EO, cocoamine 5 EO, Dowanol DB Demulse DLN 532 CE, Tween 80, Demulse DLN 622 EG, Span 20, Diacid 1550, decyl alcohol 4 EO, dipropyleneglycol methyl ester, sodium lauryl sulfate, sodium dodecyl sulfate, sodium xylenesulfonate, and Tergitol NP6.

The present composition can have the form of a solution, a solid, or an emulsion. It is preferred that the composition is in the form of an emulsion, and an oil-in-water emulsion is particularly preferred.

When the composition is an oil-in-water emulsion, it can comprise from about 2% to about 15% of a terpene, from about 1% to about 20% of a surfactant, all by weight, with the balance including water, or preferably from about 3% to about 10% of a terpene, from about 4% to about 12% of a surfactant, all by weight, with the balance including water, or more preferably, from about 3% to about 10% by weight of d-limonene, from about 4% to about 12% by weight of a surfactant comprising one or more of oleyl alcohol 10 EO, Tween 20, stearyl alcohol 20 EO, castor oil 80 EO, castor oil 30 EO, PEG 400 Dioleate, tallow amine 5 EO, Burco TME-S, coconut diethanolamide, Ethfac 161, cocoamine 2 EO, cocoamine 5 EO, Dowanol DB Demulse DLN 532 CE, Tween 80, Demulse DLN 622 EG, Span 20, Diacid 1550, decyl alcohol 4 EO, dipropyleneglycol methyl ester, sodium lauryl sulfate, sodium dodecyl sulfate, sodium xylenesulfonate, and Tergitol NP6, with the balance including water.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples all percentages are given on a weight basis unless otherwise indicated.

Example 1

This example illustrates formulations of several embodiments of the terpene and surfactant oil-in-water emulsion of the present invention.

Emulsions A-Q were prepared by first dispersing the surfactants in water, followed by addition of the terpene with vigorous mixing.

|  | Wt % |
|---|---|
| Emulsion A: (HLB 14.2) | |
| d-limonene | 5.0 |
| oleyl alcohol 10 EO | 4.5 |
| Tween 20 | 3.0 |
| water | balance |
| Example B (HLB 12.2) | |
| d-limonene | 5.0 |
| oleyl alcohol 10 EO | 6.75 |
| Span 20 | 0.75 |
| water | balance |
| Example C (HLB 15.5) | |
| d-limonene | 5.0 |
| hexadecene | 5.0 |
| stearyl alcohol 20 EO | 15.0 |
| castor oil 80 EO | 5.0 |
| water | balance |
| Example D (HLB 15.5) | |
| d-limonene | 5.0 |
| isoparaffin | 5.0 |
| stearyl alcohol 20 EO | 15.0 |
| castor oil 80 EO | 5.0 |
| water | balance |
| Example E | |
| d-limonene | 10.0 |
| Tergitol NP6 | 6.0 |
| Diacid 1550 | 4.0 |
| dipropyleneglycol methyl ester | 2.0 |
| water | balance |
| Example F | |
| d-limonene | 5.0 |
| Diacid 1550 | 3.0 |
| decyl alcohol 4 EO | 3.0 |
| dipropyleneglycol methyl ester | 2.0 |
| water | balance |
| Example G | |
| d-limonene | 5.0 |
| Dowanol DB | 2.0 |
| Demulse DLN 532 CE | 8.0 |
| water | balance |
| Example H | |
| d-limonene | 5.0 |
| Dowanol DB | 5.0 |
| Demulse DLN 622 EG | 5.0 |
| water | balance |
| Example I (HLB 10.2) | |
| d-limonene | 10.0 |
| Span 20 | 3.75 |
| Tween 80 | 1.25 |
| water | balance |
| Example J | |
| d-limonene | 5.0 |
| Cocoamine 2 EO | 3.5 |
| Cocoamine 5 EO | 3.5 |
| water | balance |
| Example K | |
| d-limonene | 5.0 |
| coconut diethanolamide | 8.0 |
| Ethfac 161 | 1.6 |
| PEG 400 Dioleate | 5.0 |
| water | balance |

-continued

| | Wt % |
|---|---|
| Example L | |
| d-limonene | 5.0 |
| Ethomeen T-15 | 4.0 |
| Burco TME-S | 4.0 |
| water | balance |
| Example M | |
| d-limonene | 7.0 |
| mineral oil | 7.0 |
| Ethomeen T-15 | 6.0 |
| Burco TME-S | 6.0 |
| water | balance |
| Example N | |
| d-limonene | 7.0 |
| castor oil 30 EO | 5.7 |
| PEG 400 dioleate | 2.7 |
| water | balance |
| Example O | |
| d-limonene | 3.0 |
| castor oil 30 EO | 5.7 |
| PEG 400 dioleate | 2.7 |
| water | balance |
| Example P | |
| d-limonene | 3.0 |
| hexadecene | 4.0 |
| castor oil 30 EO | 5.7 |
| PEG 400 dioleate | 2.7 |
| water | balance |
| Example Q | |
| d-limonene | 30.0 |
| polyacrylic acid | 0.2 |
| triethanolamine | 0.3 |
| water | balance |

Example 2

This illustrates the effect of the addition of a d-limonene emulsion on the rate of $CO_2$ evolution in the fermentation of glucose by brewer's yeast.

A mixture of d-glucose (1 gram) was mixed with 14 ml of distilled water in each of six flasks. In each of six separate flasks, a sample of brewer's yeast (1 gram of *Saccharomyces cerevisiae*, Muntons dry brewer's yeast, available from Muntons PLC, Cedars Maltings, Stowmarket, Suffolk, IP14 2AG UK) was mixed with 10 g distilled water for 30 minutes at 30° C. The yeast mixtures were added to the glucose solutions and the resulting mixtures (24 ml in each of six flasks) were mixed for 5 minutes. Two flasks (1 and 2) were blanks (having no terpene/surfactant emulsion), and various amounts of a terpene/surfactant emulsion was added to the remaining four flasks. Two flasks (3 and 4) each contained 25 ppm by weight of Emulsion O, as shown in Example 1, and the remaining two flasks (5 and 6) each had 50 ppm of the same emulsion.

To start the test, 3 ml of the yeast/glucose mixture in each flask was taken up in a 5 ml syringe with 1.0 ml of air and each syringe was attached to a respirometer (See, "Yeast on the rise: Investigative study of fermentation in the introductory biology curriculum", www.marietta.edu (Jun. 13, 2006)). The time of attachment of the syringes to the respirometer was taken to be time zero. Gas (carbon dioxide) evolution was measured for each syringe by reading the height of a bead of water in the respirometer gas collection tube. The $CO_2$ evolution as a function of time for each of the six syringes is shown in Table 1.

TABLE 1

$CO_2$ evolution as a function of time for fermentation media with different levels of a terpene/surfactant emulsion.

| | $CO_2$ production (ml) | | | | | |
|---|---|---|---|---|---|---|
| Time (min) | Syringe 1 (blank) | Syringe 2 (blank) | Syringe 3 (25 ppm) | Syringe 4 (25 ppm) | Syringe 5 (50 ppm) | Syringe 6 (50 ppm) |
| 0 | 0 | 0 | 0 | 0 | 0 | 0 |
| 1 | 0.04 | 0.03 | 0.08 | 0.07 | 0.03 | 0.03 |
| 2 | 0.09 | 0.09 | 0.16 | 0.14 | 0.06 | 0.06 |
| 3 | 0.14 | 0.14 | 0.25 | 0.22 | 0.1 | 0.095 |
| 4 | 0.19 | 0.19 | 0.34 | 0.3 | 0.14 | 0.13 |
| 5 | 0.25 | 0.25 | 0.42 | 0.38 | 0.19 | 0.18 |
| 6 | 0.3 | 0.3 | 0.5 | 0.45 | 0.25 | 0.22 |
| 7 | 0.34 | 0.36 | 0.58 | 0.53 | 0.32 | 0.29 |
| 8 | 0.39 | 0.42 | 0.66 | 0.61 | 0.39 | 0.36 |
| 9 | 0.44 | 0.47 | 0.74 | 0.7 | 0.46 | 0.45 |
| 10 | 0.48 | 0.53 | 0.84 | 0.79 | 0.53 | 0.54 |
| 11 | 0.53 | 0.58 | 0.93 | 0.88 | 0.59 | 0.63 |
| 12 | 0.57 | 0.62 | 1.02 | 1.03 | 0.64 | 0.72 |
| 13 | 0.63 | 0.67 | 1.12 | 1.14 | 0.7 | 0.82 |
| 14 | 0.68 | 0.73 | 1.22 | 1.2 | 0.76 | 0.93 |
| 15 | 0.73 | 0.79 | 1.32 | 1.3 | 0.83 | 1.04 |
| 16 | 0.79 | 0.84 | 1.42 | 1.41 | 0.9 | 1.2 |
| 17 | 0.84 | 0.9 | 1.53 | 1.53 | 1.06 | 1.27 |
| 18 | 0.89 | 0.95 | 1.64 | 1.63 | 1.13 | 1.39 |
| 19 | 0.95 | 1.01 | 1.73 | 1.75 | 1.21 | 1.51 |
| 20 | 1.01 | 1.06 | 1.84 | 1.85 | 1.28 | 1.63 |
| 21 | 1.08 | 1.13 | — | — | 1.35 | 1.75 |
| 22 | 1.13 | 1.19 | — | — | — | 1.88 |
| 23 | 1.19 | 1.26 | — | — | — | — |
| 24 | 1.25 | 1.32 | — | — | — | — |
| 25 | 1.32 | 1.41 | — | — | — | — |

TABLE 1-continued

CO$_2$ evolution as a function of time for fermentation
media with different levels of a terpene/surfactant emulsion.

| Time (min) | CO$_2$ production (ml) | | | | | |
|---|---|---|---|---|---|---|
| | Syringe 1 (blank) | Syringe 2 (blank) | Syringe 3 (25 ppm) | Syringe 4 (25 ppm) | Syringe 5 (50 ppm) | Syringe 6 (50 ppm) |
| Avg. CO$_2$ evolution rate (ml/min) | 0.054 | | 0.093 | | 0.076 | |

This data is also shown in FIG. 1, where it can be seen that all fermentations to which the terpene/surfactant emulsion had been added evolved CO$_2$ at a faster rate than the blank fermentations without the emulsion. In fact, at 20 minutes after the start of the test, the samples having 25 ppm of the emulsion had evolved over 75% more CO$_2$ than the samples without the emulsion. While gas evolution for the samples having 50 ppm of the emulsion was not quite as high as in the samples having 25 ppm of the emulsion, it was higher than for the blank samples.

It is believed that this shows the efficacy of the terpene/surfactant emulsion in increasing the rate of an ethanol fermentation by a yeast.

Example 3

This example illustrates the effectiveness of an embodiment of the present method in increasing the viability of yeast and improving the maintenance requirements in a commercial ethanol plant.

These tests were run in a commercial fuel ethanol plant that used corn as the substrate.

Different amounts of the terpene/surfactant emulsion of Example N of Example 1 were added to commercial fermenters at different stages of batch fermentations. In test "A", 50 ppm of Example N was added to the medium in a fermenter at a time that was about 3 hours before the end of the fermentation. Total batch fermentation time was usually about 10-120 hours. At the time of addition of the emulsion, total yeast count was 282 (yeast count by light microscopy per unit area) with viable yeast count of 221 (21% dead yeasts), and where 28.5% of the live yeasts were budding. At the end of the fermentation, 3 hours later, total yeast count was 224 with a viable yeast count of 192 (14% dead yeasts), and where 25% of the live yeasts were budding. In a normal fermentation under the same conditions, except without the addition of the terpene/surfactant emulsion, percent budding at the end of the fermentation would have been expected to be about 10%. Accordingly, it was seen that addition of the emulsion in the final stages of the fermentation increased the number of budding yeasts, indicating improved health of the live yeasts remaining at the end of the fermentation.

In general, the healthier the yeasts at the end of a fermentation batch, the less yeast replacement is necessary, with a resulting savings in cost of operations.

In another test, a 100 ppm of a terpene/surfactant emulsion having the composition of Example N of Example 1 was added to the medium in a production fermenter at a point that was about 12 hours before the end of the fermentation. At the time of addition of the emulsion, total yeast count was 300 (per unit area by light microscopy) with viable yeast count of 274 (9% dead yeasts), and where 20% of the live yeasts were budding. At the end of the fermentation, 12 hours later, total yeast count was 269 with a viable yeast count of 242 (10% dead yeasts), and where 23% of the live yeasts were budding. These results were similar to the first test and showed that addition of the emulsion in the middle stages of the fermentation increased the number of budding yeasts, indicating improved health of the live yeasts remaining at the end of the fermentation.

In both tests, final ethanol concentration in the medium was about 12.3% weight/volume, which was normal for the fermentations under the same conditions, but without the terpene/surfactant emulsion.

In another series of fermentation batches, some of the batches received additions of the terpene/surfactant emulsion and others did not. However, at the end of a week of operation, it was noticed that the fill header for the fermenters was relatively clean. The planned shutdown for normal maintenance was postponed for several more days before a shutdown for cleaning would be necessary. This is believed to show that the use of the terpene/surfactant can extend the period between shutdowns for cleaning. This would have the effect of increasing the overall rate of production of ethanol from the plant.

Example 4

This example illustrates the improvement in the utilization rate of sugar in a yeast fermentation of glucose provided by a combination of d-limonene and surfactant.

D-glucose (5 g) was dissolved in 45 g of tap water, followed by 0.4 g of Muntons dry brewers yeast and this mixture was allowed to mix for 30 minutes in the presence of air. The sugar/yeast/water mixture was then taken up in a 60 ml syringe with 1.0 cc of airspace and lightly capped. This procedure was repeated three times except that the composition of Example P was added to the mixture just prior to taking the mixtures up in the three syringes in amounts of 20, 50 and 100 ppm by weight. Consequently, there were four syringes, one with zero Example P, one having 20 ppm, one having 50 ppm, and one having 100 ppm. The four syringes were allowed to sit undisturbed for 78 hours at room temperature.

After 78 hours, a portion of the mixture in each syringe was withdrawn and filtered through a 25 mm Teflon syringe filter (5 micron) and percent Brix was determined as a measure of the amount of sugar in the mixture. The results were as shown in Table 2.

TABLE 2

Sugar remaining in fermentations at 78 hours.

| Amount of Composition P in sample (ppm by weight) | Percent Brix at start | Percent Brix at 78 hours |
|---|---|---|
| 0 | 9.0 | 5.4 |
| 20 | 9.0 | 5.4 |
| 50 | 9.0 | 5.0 |
| 100 | 9.0 | 4.8 |

The data showed that the presence of the composition of Example P resulted in increased sugar utilization by the yeasts at the 50 and 100 ppm levels. By way of example, 46.6% sugar conversion was seen in the sample containing 100 ppm of the terpene/surfactant composition of Example P compared with 40% conversion in the blank.

Example 5

This example illustrate the effectiveness of an embodiment of the present method in increasing the viable yeast plate counts and yeast budding index in laboratory corn mash fermentations.

Theses tests were run in a laboratory fermentation bioreactor setup using a gelatinized and enzyme degraded corn mash as the feed substrate. All conditions were set to duplicate the commercial scale anaerobic fermentation process. Different amounts of the terpene/surfactant emulsion of Example N of Example 1 were added to parallel fermentation reactions. Samples of each fermentation broth were collected after 6 hours, 12 hours, and 48 hours reaction time for analysis, and plate counts were done to measure the yeast populations. Analysis of the 6 hour samples showed that the fermentation reactions treated with 100 ppm and 200 ppm of Example N contained 50% higher levels of active viable yeast, when compared to the control test with no Example N added. The results of analysis at 12 hours were similar, with approximately 50% increased viable yeast counts at both 100 and 200 ppm dosage of Example N, compared to the control test with no Example N added. The results from samples collected after 48 hours of total fermentation time were similar, with nearly 50% increased levels of viable yeast counts at both 100 and 200 ppm dosage of Example N, compared to he control test with no Example N added. Microscopic analysis of the fermentation of broth samples indicated a higher percent of viable yeasts and a higher percent budding of the yeasts present, in samples from the fermentation broths treated with 100-200 ppm of Example N when compared to the control samples from fermentation broth without Example N added.

The increased viable yeast counts are expected to offer benefits such as increased process yield, increased rate of fermentation, reduced competition from bacteria, reduced undesirable side products, improved yeast regeneration and yield, and/or improved operating conditions.

All references cited in this specification, including without limitation all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions by those of ordinary skill in the art without departing from the scope of the invention, it is intended that all matter contained in the above description and shown in the accompanying drawing shall be interpreted as illustrative and not in a limiting sense. In addition it should be understood that aspects of the various embodiments may be interchanged both in whole or in part.

What is claimed is:

1. A method of increasing the overall rate of ethanol production by a *Saccharomyces* spp. yeast during fermentation of a feedstock substrate consisting essentially of corn in the fermentation medium, the method comprising adding an emulsion comprising a monoterpene and a surfactant to said fermentation medium in an amount sufficient to improve the viability of said yeast, thereby increasing the overall rate of ethanol production as the primary product of fermentation.

2. The method according to claim 1, wherein said *Saccharomyces* spp. yeast is *Saccharomyces cerevisiae*.

3. The method according to claim 1, wherein the monoterpene is limonene.

4. The method according to claim 1, wherein the monoterpene is an isolated and purified monoterpene.

5. The method according to claim 1, wherein the surfactant selected from ethoxylated alcohols, ethoxylated carbohydrates, ethoxylated vegetable oils, polyethyleneglycols (PEG), polypropylene glycols (PPG), monoesters and diesters of PEG and PPG, ethoxylated amines, fatty acids, ethoxylated fatty acids, fatty amides, and fatty diethanolamides.

6. The method according to claim 5, wherein the surfactant has an HLB value between about 7 and about 25.

7. The method according to claim 5, wherein the surfactant has an HLB value between about 9 and about 18.

8. The method according to claim 5, wherein the surfactant has an HLB value between about 11 and about 16.

9. The method according to claim 5, wherein the surfactant is selected from one or more oleyl alcohol 10 EO, Tween 20, stearyl alcohol 20 EO, castor oil 80 EO, castor oil 30 EO, PEG 400 Dioleate, tallow amine 5 EO, Burco TME-S, coconut diethanolamide, Ethfac 161, cocoamine 2 EO, cocoamine 5 EO, Dowanol DB Demulse DLN 532 CE, Tween 80, Demulse DLN 622 EG, Span 20, Diacid 1550, decyl alcohol 4 EO, dipropyleneglycol methyl ester, sodium lauryl sulfate, sodium dodecyl sulfate, sodium xylenesulfonate, and Tergitol NP6.

10. The method according to claim 1, wherein the emulsion comprising the monoterpene and the surfactant is added to the fermentation medium before inoculation with the microorganism.

11. The method according to claim 1, wherein the emulsion comprising the monoterpene and the surfactant is added to the fermentation medium during the first one-third of the fermentation.

12. The method according to claim 1, wherein the emulsion comprising the monoterpene and the surfactant is added to the fermentation medium during the middle one-third of the fermentation.

13. The method according to claim 1, wherein the emulsion comprising the monoterpene and the surfactant is added to the fermentation medium during the final one-third of the fermentation.

14. The method according to claim 1, wherein the emulsion comprising the monoterpene and the surfactant is added to the fermentation medium in two or more increments during the fermentation.

15. The method according to claim 1, wherein the emulsion is an oil-in-water emulsion.

16. The method according to claim 1, wherein the emulsion comprises from about 1% to about 70% of the monoterpene and, from about 0.2% to about 25% of a surfactant, all by weight, with the balance including water.

17. The method according to claim 1, wherein the emulsion comprises from about 2% to about 20% of the monoterpene and from about 1% to about 20% of the surfactant, all by weight, with the balance including water.

18. The method according to claim 1, wherein the emulsion comprises from about 3% to about 15% of the monoterpene and from about 2% to about 10% of the surfactant, all by weight, with the balance including water.

19. The method according to claim 1, wherein the emulsion comprising the monoterpene and the surfactant is added to the fermentation medium in an amount of from about 0.1 ppm to about 1000 ppm, by weight.

20. The method according to claim 19, wherein the emulsion comprising the monoterpene and the surfactant is added to the fermentation medium in an amount of from about 1 ppm to about 100 ppm, by weight based on the fermentation medium.

* * * * *